United States Patent [19]

Schmerling

[11] 4,005,125

[45] Jan. 25, 1977

[54] PREPARATION OF HALOALKYL ESTERS

[75] Inventor: Louis Schmerling, Riverside, Ill.

[73] Assignee: Universal Oil Products Company, Des Plaines, Ill.

[22] Filed: May 5, 1975

[21] Appl. No.: 574,493

[52] U.S. Cl. .................... 260/476 R; 260/410.9 R; 260/475 R; 260/485 H; 260/486 H; 260/496
[51] Int. Cl.² ........................................ C07C 67/24
[58] Field of Search ....... 260/485 H, 476 R, 475 R, 260/496, 486 H, 410.9 R

[56] References Cited

UNITED STATES PATENTS 2,513,504  7/1950  McFarlane .................... 260/476 R Primary Examiner—Jane S. Myers
Attorney, Agent, or Firm—James R. Hoatson, Jr.; Raymond H. Nelson; William H. Page, II

[57] ABSTRACT

Haloalkyl esters are prepared by reacting a saturated cyclic ether with a carboxylic acid or anhydride thereof and a hydrogen halide or hydrohalic acid in the presence of a Friedel-Crafts catalyst.

13 Claims, No Drawings

PREPARATION OF HALOALKYL ESTERS

BACKGROUND OF THE INVENTION

It has been known in the past that saturated cyclic ethers such as tetrahydrofuran or tetrahydropyran may be converted to esters by treatment with a carboxylic acid anhydride in the presence of certain catalytic compositions of matter. For example, it has been stated in the prior art that the opening of tetrahydrofuran and tetrahydropyran rings by reaction with acetic anhydride was accomplished readily only in the presence of zinc chloride at a reaction temperature of about 100° C. or more. Other prior art methods of accomplishing the opening of the rings employed catalysts such as boron trifluoride, sulfuric acid, etc. Likewise, it has also been disclosed in the prior art that tetrahydrofuran undergoes no cleavage even after being heated under reflux for 5 hours with stannic chloride or after being treated with acetic acid and stannic chloride at higher reaction temperatures. Other prior art discloses that acyl halides may also be employed to effect the ring cleavage of tetrahydrofuran or tetrahydropyran. However, a disadvantage in utilizing these compounds is that such compounds must be first prepared from the acid before being reacted with the cyclic ether. The preparation of these compounds usually entails the reaction of a inorganic halide such as phosphorus pentachloride and the desired acid. As will hereinafter be shown in greater detail, it has now been discovered that haloalkyl esters may be prepared by converting saturated cyclic ethers such as the tetrahydrofurans or tetrahydropyrans by reaction with a carboxylic acid or anhydride thereof and a hydrogen halide as such or in aqueous solution in the presence of a Friedel-Crafts type catalyst.

This invention relates to a process for the preparation of haloalkyl esters. More specifically, the invention is concerned with a process for preparing haloalkyl esters by reacting a saturated cyclic ether with a carboxylic acid or anhydride thereof and a hydrogen halide in the presence of a metal halide catalyst to prepare the desired compound.

Haloalkyl esters which may be prepared according to the process of this invention will find a wide variety of uses in the chemical field. For example, the aforementioned haloalkyl esters may be used as intermediates for the preparation of detergents or agents for decreasing the evaporation of water. As a specific example of this type of use, a haloalkyl ester such as 4-chlorobutyl acetate which has been prepared by reacting tetrahydrofuran with acetic acid and hydrochloric acid may be reacted with a long chain alkylaromatic compound such as n-octylbenzene to form a product which can be used as such or which may be converted to the sulfuric ester by treatment with sulfuric acid or to a non-ionic detergent in the form of a polyethylene ether via reaction with ethylene oxide.

It is therefore an object of this invention to provide a process for the preparation of haloalkyl esters.

A further object of this invention is to provide a process for preparing haloalkyl esters by reacting a carboxylic acid or anhydride thereof and a hydrogen halide or hydrohalic acid with a compound such as tetrahydropyran.

In one aspect an embodiment of this invention resides in a process for the preparation of a haloalkyl ester which comprises reacting a carboxylic acid or anhydride thereof and a hydrogen halide or hydrohalic acid with a saturated cyclic ether in the presence of a Friedel-Crafts catalyst at reaction conditions, and recovering the resultant haloalkyl ester.

A specific embodiment of this invention is found in a process for the preparation of a haloalkyl ester which comprises reacting tetrahydrofuran with acetic acid and hydrochloric acid in the presence of stannic chloride at a temperature in the range of from about 20° to about 250° C. and recovering the resultant 4-chlorobutyl acetate.

Other objects and embodiments will be found in the following further detailed description of the present invention.

As hereinbefore set forth, the present invention is concerned with a process for the preparation of haloalkyl esters by reacting a saturated cyclic ether with a carboxylic acid and a hydrogen halide in the presence of a metal halide catalyst at reaction conditions.

Examples of saturated cyclic ethers which may be utilized as one of the starting materials in the process of this invention will include both 4 and 5 carbon-atom-membered rings, specific examples of these saturated ethers including tetrahydrofuran, tetrahydropyran, as well as alkyl- and halogen-substituted tetrahydrofurans and tetrahydropyrans in which the alkyl substituents may contain from 1 to about 6 carbon atoms such as 2-methyltetrahydrofuran, 2-ethyltetrahydrofuran, 2-propyltetrahydrofuran, 2-isopropyltetrahydrofuran, 2-n-butyltetrahydrofuran, 2-sec-butyltetrahydrofuran, 2-isobutyltetrahydrofuran, 2-t-butyltetrahydrofuran, 3-methyltetrahydrofuran, 3-ethyltetrahydrofuran, 3-propyltetrahydrofuran, 2-n-pentyltetrahydrofuran, 2-sec-pentyltetrahydrofurans, 2-n-hexyltetrahydrofuran, 2-sec-hexyltetrahydrofuran, 2-chlorotetrahydrofuran, 2-bromotetrahydrofuran, 2,3-dimethyltetrahydrofuran, 2,4-dimethyltetrahydrofuran, 2,5-dimethyltetrahydrofuran, 2,3-diethyltetrahydrofuran, 2,4-diethyltetrahydrofuran, 2,4-diisopropyltetrahydrofuran, 2,5-di-n-butyltetrahydrofuran, 2-methyltetrahydropyran, 2-ethyltetrahydropyran, 2-propyltetrahydropyran, 2-isopropyltetrahydropyran, 2-n-butyltetrahydropyran, 2-isobutyltetrahydropyran, 2-sec-butyltetrahydropyran, 2-t-butyltetrahydropyran, 3-methyltetrahydropyran, 3-ethyltetrahydropyran, 3-propyltetrahydropyran, 4-methyltetrahydropyran, 4-ethyltetrahydropyran, 4-propyltetrahydropyran, 2-n-pentyltetrahydropyran, 2-sec-pentyltetrahydropyran, 2-n-hexyltetrahydropyran, 2-sec-hexyltetrahydropyran, 2-chlorotetrahydropyran, 2-bromotetrahydropyran, 2,3-dimethyltetrahydropyran, 2,3-diethyltetrahydropyran 2,4-dimethyltetrahydropyran, 2,4 -diisopropyltetrahydropyran, 2,5-dimethyltetrahydropyran, 2,6-dimethyltetrahydropyran, etc. It is to be understood that these saturated cyclic ethers are only representative of the class of compounds which may be employed as one of the reactants, and that the present invention is not necessarily limited thereto.

The aforementioned saturated cyclic ethers are reacted with carboxylic acids, said carboxylic acids containing from 1 to about 20 carbon atoms and which may be saturated, unsaturated, aromatic, monobasic, or polybasic in nature. Specific examples of the acids which may be reacted with the saturated cyclic ethers will include the aliphatic monobasic fatty acids such as formic acid, acetic acid, propionic acid, butyric acid, valeric acid, caproic acid, oenanthylic acid, caprylic acid, pelargonic acid, capric acid, undecylic acid, lauric acid, tridecoic acid, myristic acid, pentadecanoic acid, palmitic acid, margaric acid, stearic acid, nondecylic acid, arachidic acid, etc.; aromatic acids such as benzoic acid, o-toluic acid, m-toluic acid, p-toluic acid, phthalic acid, isophthalic acid, terephthalic acid, 2-phenylacetic acid, 3-phenylpropionic acid, 4-phenylbutyric acid, 5-phenylvaleric acid, etc.; unsaturated monobasic acids such as the acrylic acid series including acrylic acid, crotonic acid, isocrotonic acid, tiglic acid, senecioic acid, hexenoic acid, teracrylic acid, oleic acid, etc.; aliphatic dibasic acids such as oxalic acid, malonic acid, succinic acid, glutaric acid, adipic acid, pimelic acid, suberic acid, azelaic acid, sebacic acid, etc.; unsaturated dibasic acids such as fumaric acid, maleic acid, glutaconic acid, criticonic acid, allylmalonic acid, allylsuccinic acid, etc. In addition to the aforementioned carboxylic acids, it is also contemplated within the scope of this invention that the anhydrides thereof may also be employed as one of the reactants in the reaction of the present invention, said anhydrides including acetic anhydride propionic anhydride, butyric anhydride, etc.; phthalic anhydride, benzoic acid anhydride, acrylic acid anhydride, crotonic acid anhydride, tiglic acid anhydride, oxalic acid anhydride, malonic acid anhydride, succinic acid anhydride, etc.; maleic acid anhydride, glutaconic acid anhydride, etc. As in the case of the saturated cyclic ethers, the aforementioned carboxylic acids and anhydrides thereof are only representative of the class of compounds which may be employed and that the present invention is not necessarily limited thereto.

In addition to the aforementioned saturated cyclic ethers and carboxylic acids, the third component of the reaction will comprise a hydrogen halide, the preferred hydrogen halides being hydrogen chloride and hydrogen bromide due to the relatively greater availability and lower cost thereof. These hydrogen halides may be employed in either the anhydrous form as gases or as aqueous solutions, for example, hydrochloric acid or hydrobromic acid, etc.

The reaction of the saturated cyclic ether with the aforementioned carboxylic acids or anhydrides thereof and the hydrogen halide or hydrohalic acid is effected in the presence of certain catalysts comprising metal halides, especially the Friedel-Crafts metal halides which are not deactivated by stoichiometric amounts of the carboxylic acids or water. Examples of this type of metal halide catalyst which may be employed will include stannic chloride, zinc chloride, ferric chloride and boron trifluoride. When effecting the reaction in the presence of these catalysts, the reaction conditions which are employed will include temperatures which may vary over a relatively wide range, said range being from about 20° up to about 250° C., the particular temperature which is utilized being dependent upon the particular catalyst which is employed in the reaction. For example, when utilizing stannic chloride as the catalyst, it is possible to effect the reaction at temperatures in the lower portion of the aforesaid range, that is, from about 20° to about 100° C. Conversely, when utilizing zinc chloride, the reaction must be effected at temperatures in the higher range, that is, temperatures in a range of from about 150° to about 250° C. must be employed. In addition to the wide range of temperatures, it is also contemplated within the scope of this invention that varying amounts of pressure may also be employed. While the reaction is preferably effected at atmospheric pressure, it is also possible to utilize superatmospheric pressures ranging up to about 100 atmospheres, the particular amount of pressure which is employed being that which is sufficient to maintain a major portion of the reactants in the liquid phase.

The process of this invention may be effected in any suitable manner and may comprise either a batch or continuous type operation. For example, when a batch type operation is used and the hydrogen halide which is employed is in aqueous form such as a hydrohalic acid, a desired quantity of each of the reactants, namely, the saturated cyclic ether, the carboxylic acid or anhydride thereof, and the hydrohalic acid are placed in an appropriate apparatus which contains the metal halide catalyst and which is provided with stirring and heating means. Alternatively the ether, carboxylic acid and hydrohalic acid may be admixed following which the catalyst, in liquid or solid form, may then be added to the reaction mixture. The mixture of the reactants and catalyst is then continuously stirred at a predetermined operating temperature within the range hereinbefore set forth for a predetermined residence time which may range from about 0.5 up to about 10 hours or more in duration. Upon completion of this time period, the reaction mixture, after reaching room temperature, is recovered and subjected to conventional means of separation and purification including filtration to remove the catalyst, washing, extracting, drying, fractional distillation, etc., whereby the desired haloalkyl ester is separated and recovered from any unreacted starting materials and/or side reaction products which may have formed. In the event that the hydrogen halide, which comprises one of the reactants of the present process, is to be utilized in gaseous form, it will be necessary to effect the reaction in an appropriate apparatus which is pressure resistant and which may comprise an autoclave of the mixing or stirring type.

It is also contemplated within the scope of this invention that the process for the formation of haloalkyl esters may also be effected in a continuous manner of operation. When this type of operation is to be employed, the reactants comprising, as hereinbefore set forth, a saturated cyclic ether, a carboxylic acid or anhydride thereof, and a hydrogen halide either in gaseous form or in aqueous form as a hydrohalic acid are continuously charged to a reaction vessel which is maintained at the appropriate operating temperature and, if so desired, pressure. The reactants may be charged to the reactor, which contains the Friedel-Crafts catalyst, through separate lines or, if so desired, one or more may be admixed prior to entry into said reactor and the resulting mixture charged thereto in a single stream. Upon completion of the desired residence time, the reactor effluent is continuously withdrawn and subjected to the conventional means of separation similar to those hereinbefore set forth, whereby the desired haloalkyl ester is separated and recovered, while any unreacted starting materials may be recycled to form a portion of the feed stock. When the catalyst such as ferric chloride which is employed to effect the reaction is in solid form, it is possible to utilize various modifications in the continuous type of operation. For example, one modification which may be utilized is to effect the continuous type of operation in a fixed bed wherein the catalyst is positioned as a fixed bed in the reaction zone and the reactants are passed over said catalyst in either an upward or downward flow. Another modification which may be employed in the process is to utilize a moving bed type of operation in which the reactants and the catalyst bed are passed through the reaction zone either concurrently or countercurrently to each other. Alternatively, a slurry type of operation may be used in which the solid catalyst is carried into the reaction zone as a slurry in one or more of the reactants.

The reactants may be present in the reaction zone in equimolar ratios although it is contemplated within the scope of this invention that the saturated cyclic ether may be present in an excess over the carboxylic acid or anhydride thereof and the hydrogen halide, the saturated cyclic ether being present in a mole ratio in the range of from about 1.1:1 to about 1.5:1 moles of saturated cylic ether per mole of carboxylic acid or anhydride thereof and hydrogen halide.

The following examples are given for purposes of illustrating the process of the present invention. However, it is not intended that said invention be limited in strict accordance therewith.

EXAMPLE I

In this example 50 grams (0.69 mole) of tetrahydrofuran and 50 grams (0.83 mole) of acetic acid along with 30 grams (0.31 mole) of concentrated hydrochloric acid were placed in an Erlenmeyer flask provided with magnetic stirring means. Following this, 15 grams of stannic chloride were added dropwise during a period of 10 minutes to the magnetically stirred mixture. Due to the exothermic reaction caused by the addition of the catalyst, the temperature rose to 40° C. After stirring for an additional 2 hours, the reaction mixture was permitted to stand for a period of 16 hours, following which it was heated to a temperature of from 62° to 64° C. and stirred for a period of 3 hours. The unreacted material was distilled from the product and the bottoms which remained consisting of 41 grams was analyzed by gas chromatography. This analysis showed that the bottoms consisted chiefly of 4-chlorobutyl acetate with a small amount of 1,4-diacetoxybutane and unreacted acetic acid.

EXAMPLE II

An additional experiment was performed in which 50 grams (0.69 mole) of tetrahydrofuran was admixed with 22 grams (0.08 mole) of stannic chloride, the addition resulting in a white precipitate. To the mixture was then added 22 grams (0.22 mole) of concentrated hydrochloric acid, said addition resulting in the dissolution of a major portion of the precipitate. The mixture was then stirred and 21 grams (0.35 mole) of acetic acid was then added dropwise during a period of 0.5 hours, the temperature of the solution being maintained in a range of from 30° to 35° C. After stirring the mixture for an additional period of 6.5 hours, the reaction product was recovered, washed with water to remove any unreacted acetic acid, hydrochloric acid and tetrahydrofuran. The product which was then recovered was analyzed by gas chromatography and found to contain 4-chlorobutyl acetate as the major product.

Likewise, if acetic anhydride is used in place of the acetic acid and hydrochloric acid is also present, the chief product will also comprise 4-chlorobutyl acetate. However, if hydrochloric acid is not added to the reaction mixture, a small amount of 4-chlorobutyl acetate will also form, the chlorine being furnished by the stannic chloride catalyst, while the chief product will comprise 1,4-diacetoxybutane.

EXAMPLE III

In this example 60 grams (0.7 mole) of tetrahydropyran and 50 grams (0.83 mole) of acetic acid are placed in an Erlenmeyer flask along with 30 grams (0.31 mole) of concentrated hydrochloric acid. The mixture is then stirred and 15 grams of stannic chloride are slowly added dropwise to the stirred solution during a period of 10 minutes. Inasmuch as the addition of the catalyst will result in an exothermic reaction, the temperature of the mixture is controlled so that it does not rise above 40° C. The mixture is stirred for a period of 2 hours, allowed to stand for a period of 16 hours and thereafter is heated to a temperature of 65° C. and stirred for an additional period of 3 hours. The reaction mixture, after removal of the unreacted material by distillation, is analyzed by gas chromatography. This analysis will disclose that the major portion of the product is 5-chloropentyl acetate.

EXAMPLE IV

To an Erlenmeyer flask provided with magnetic stirring means is added 50 grams (0.69 mole) of tetrahydrofuran and 13 grams (0.08 mole) of ferric chloride. Following this, 12 grams (0.25 mole) of hydrobromic acid is added and the mixture is stirred. To the stirred product is then added 24.5 grams (0.33 mole) of propionic acid, the addition being effected by adding said acid dropwise during a period of 0.5 hours. Upon completion of the addition of the acid, the mixture is stirred for an additional period of 8 hours and the reaction product is then recovered. After washing the product with water to remove any unreacted starting materials, the product is subjected to gas chromatography analysis, said analysis disclosing that the major portion of the product comprises 4-bromobutyl propionate.

EXAMPLE V

In this example 60 grams (0.7 mole) of tetrahydropyran and 85 grams (0.7 mole) of benzoic acid along with 30 grams (0.31 mole) of concentrated hydrochloric acid are placed in an Erlenmeyer flask, said flask being provided with magnetic stirring means. Following this, 15 grams of stannic chloride are slowly added dropwise to the magnetically stirred solution of the mixture during a period of 0.25 hours, the temperature of the mixture rising to about 40° C. due to the exothermic nature of the reaction. The mixture is then filtered for an additional period of 2 hours, allowed to stand for a period of 16 hours and is then heated to a temperature of 65° C. The mixture is stirred at this temperature for a period of 5 hours following which the unreacted starting materials are removed by distillation. The bottoms remaining is analyzed by gas chromatography and found to consist mainly of 5-chloropentyl benzoate.

I claim as my invention:

1. A process for the preparation of a haloalkyl ester which comprises reacting a hydrocarbon carboxylic acid containing from 1 to about 20 carbon atoms or anhydride thereof and a hydrogen halide or hydrohalic acid with a saturated cyclic ether selected from the group consisting of tetrahydrofuran, tetrahydropyran, halogen-substituted tetrahydrofurans and tetrahydropyrans and alkyl-substituted tetrahydrofurans and tetrahydropyrans in which the alkyl contains from 1 to about 6 carbon atoms in the presence of a Friedel-Crafts metal halide catalyst at a temperature of from about 20° to about 250° C., and recovering the resultant haloalkyl ester.

2. The process of claim 1 further characterized in that said catalyst is selected from the group consisting of stannic chloride, zinc chloride, ferric chloride and boron trifluoride.

3. The process as set forth in claim 1 in which said saturated cyclic ether is tetrahydrofuran.

4. The process as set forth in which said saturated cyclic ether is tetrahydropyran.

5. The process as set forth in claim 1 in which said Friedel-Crafts catalyst is stannic chloride.

6. The process as set forth in claim 1 in which said Friedel-Crafts catalyst is ferric chloride.

7. The process as set forth in claim 1 in which said hydrohalic acid is hydrochloric acid.

8. The process as set forth in claim 1 in which said hydrohalic acid is hydrobromic acid.

9. The process as set forth in claim 1 in which said carboxylic acid is acetic acid, said hydrohalic acid is hydrochloric acid, said saturated cyclic ether is tetrahydrofuran, said Friedel-Crafts catalyst is stannic chloride, and said haloalkyl ester is 4-chlorobutyl acetate.

10. The process as set forth in claim 1 in which said carboxylic acid is acetic anhydride, said hydrohalic acid is hydrochloric acid, said saturated cyclic ether is tetrahydrofuran, said Friedel-Crafts catalyst is stannic chloride, and said haloalkyl ester is 4-chlorobutyl acetate.

11. The process as set forth in claim 1 in which said carboxylic acid is acetic acid, said hydrohalic acid is hydrochloric acid, said saturated cyclic ether is tetrahydropyran, said Friedel-Crafts catalyst is stannic chloride and said haloalkyl ester is 5-chloropentyl acetate.

12. The process as set forth in claim 1 in which said carboxylic acid is propionic acid, said hydrohalic acid is hydrobromic acid, said saturated cyclic ether is tetrahydrofuran, said Friedel-Crafts catalyst is ferric chloride and said haloalkyl ester is 4-bromobutyl propionate.

13. The process as set forth in claim 1 in which said carboxylic acid is benzoic acid, said hydrohalic acid is hydrochloric acid, said saturated cyclic ether is tetrahydropyran, said Friedel-Crafts catalyst is stannic chloride and said haloalkyl ester is 5-chloropentyl benzoate.

* * * * *